United States Patent [19]
Allen et al.

[11] Patent Number: 5,354,442
[45] Date of Patent: Oct. 11, 1994

[54] MATRIX MODIFICATION IN THE ELECTROPHORETIC SEPARATION OF NUCLEIC ACIDS

[75] Inventors: Robert C. Allen, Palms, S.C.; Dennis J. Reeder, Gaithersburg, Md.

[73] Assignee: The United States of America as represented by the Secretary of the Commerce, Washington, D.C.

[21] Appl. No.: 886,289

[22] Filed: May 21, 1992

[51] Int. Cl.$^5$ ................ G01N 27/26; G01N 27/447
[52] U.S. Cl. ........................ 204/182.8; 204/299 R
[58] Field of Search ...................... 204/182.8, 299 R

[56] References Cited

U.S. PATENT DOCUMENTS

| | | |
|---|---|---|
| 4,673,641 | 6/1987 | George et al. . |
| 4,683,194 | 7/1987 | Saiki et al. . |
| 4,746,551 | 5/1988 | Allen et al. ............... 427/389.7 |
| 4,791,063 | 12/1988 | Hou et al. . |
| 4,879,214 | 11/1989 | Kornher et al. . |
| 4,975,165 | 12/1990 | Brandley . |
| 4,993,368 | 2/1991 | Goodman et al. . |
| 5,059,654 | 10/1991 | Hou et al. . |
| 5,068,176 | 11/1991 | Vijg et al. . |
| 5,159,049 | 10/1992 | Allen ............................ 524/56 |

OTHER PUBLICATIONS

Bertold v. Radola et al. "Preparation of rehydratable polyacrylamide gels and their application in ultra-thin-layer isoelectric focusing" Electrophoresis 1986, 7 (1986) 28–40.

Robert C. Allen and George M. Graves "Rehydratable Gels: A Potential Reference Standard Support for Electrophoresing PCR-Amplified DNA" Biotechnology, vol. 8 (Dec. 1990) 1288–1290.

Allen, R. C. et al. "Tailoring DNA Resolution in Polyacrylamide Gels with Electrochemistry and Pulsed Constant Power Given Jul. 6, 1989", Washington, D.C. (1 page).

*Primary Examiner*—John Niebling
*Assistant Examiner*—John S. Starsiak, Jr.
*Attorney, Agent, or Firm*—Lowe, Price, LeBlanc & Becker

[57] ABSTRACT

The present invention is a method for enhancing the separation of polynucleotides or polypeptides of various chain lengths or a mixture of polynucleotides and polypeptides of various chain lengths using electrophoretic processes to sharpen sample component zones and produce maximum resolution of electrophoretically separated macromolecules by modifying the matrix of electrophoretic gel.

10 Claims, 11 Drawing Sheets

MATRIX MODIFICATION IN THE ELECTROPHORETIC SEPARATION OF NUCLEIC ACIDS

TECHNICAL FIELD

The present invention relates to an improved method for the separation of a wide variety of sizes of macromolecules such as polypeptides and polynucleotides using an improved electrophoretic support and medium. The present invention also relates to an improved pulsed constant power method of electrophoresis for separating proteins and nucleic acids.

BACKGROUND OF THE INVENTION

Polyacrylamide and other acrylamide-based polymers are used as support matrices for various electrophoretic processes, including separation procedures such as isoelectric focusing, conventional zone, capillary zone, or discontinuous zonal electrophoresis. Various modifications in the pore size of the acrylamide support medium are often required for separations based on either the charge, size, or both, of macromolecules of biological origin. For example, low resolution simple charge separations of the plasma proteins may be made on media such as agarose, cellulose acetate and paper that contain pore sizes too large to sieve the molecules.

High resolution separations of macromolecules based on size require a support medium where the pore size can be varied to exert a sieving or retardation effect, on the macromolecules as they migrate in the electrical field. Such separations require a system wherein the pore size may be varied or produced with a graduated pore size. This is commonly done using polyacrylamide gels or acrylamide derivatives, where the pore size may be varied by varying the monomer concentration. An electrophoretic gel having a single pore size will not resolve many of the macromolecules present in a complex mixture.

The article Allen et al, "Rehydratable Gels: A Potential Reference Standard Support for Electrophoresing PCR-Amplified DNA" published in Biotechnology, Vol. 8, Dec. 1990 by the present Applicants has indicated that rehydratable gels can be modified after their formation by adding specific amounts of one or more alcohols, polyols or monosaccharides. The matrix modifiers were added to preformed polyacrylamide gels and were used to separate various macromolecules.

Accordingly, there is a continued need in this art for an improved method for resolving mixtures of biological macromolecules using a modified electrophoretic support to increase the resolution of macromolecules such as polynucleotides and polypeptides. Further, there is a need in this art to further improve the resolution of electrophoretic support media whose matrix has been modified to enhance the separations of macromolecules and individualization process of various biological materials.

DISCLOSURE OF THE INVENTION

Accordingly, it is an object of the present invention to provide an improved process for electrophoretic separation by a modification of matrices to allow multiple types of electrophoretic separation selected from the group consisting of continuous zone electrophoretic separation, multi-zonal electrophoretic separation, and isoelectric focusing electrophoretic separation. This process comprises treating the support matrix of the electrophoretic support with a matrix modifier selected from the group consisting of an alcohol, a polyol, or a monosaccharide in an amount effective to retard the migration of the nucleic acids or proteins that would normally not unstack from a moving boundary in untreated matrixes of the same pore size. It also includes increasing the concentration of said modifiers in a wide range of buffer ionic strengths to further reduce the relative mobility of said macromolecules and further increase the resolution range of the support.

It is another object of the present invention to provide an improved method of separating macromolecules using pulsed constant power electrophoresis procedures in combination with an electrophoretic support whose matrix has been modified with an alcohol, a polyol, or a monosaccharide to improve the degree of separation of a complex mixture of macromolecules selected from the group consisting of polynucleotides, polypeptides, or a mixture thereof.

BEST MODE FOR CARRYING OUT THE INVENTION

Figure 1A:
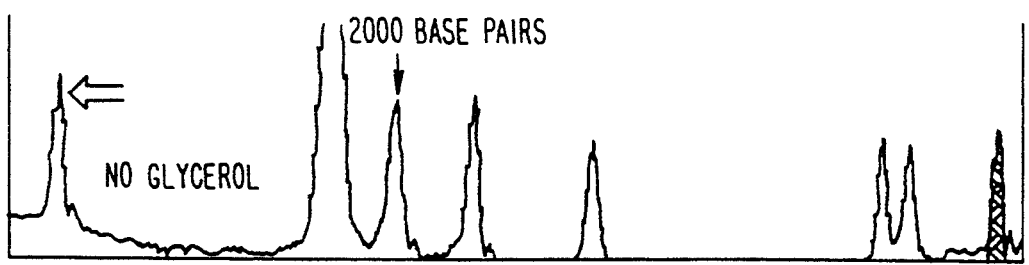
FIG. 1 shows the effects of various concentrations of glycerol upon a polyacrylamide gel and its resolution of nucleotides of different lengths.
Figure 1B:
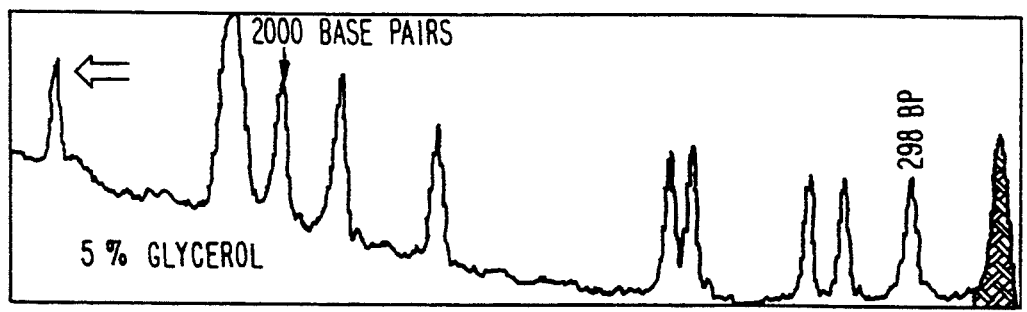
Figure 1C:
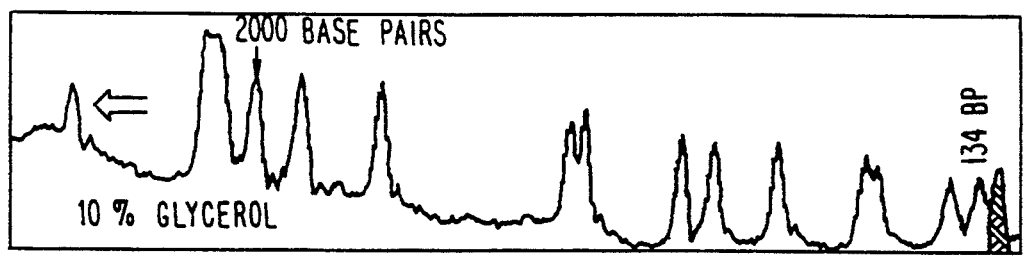
Figure 1D:
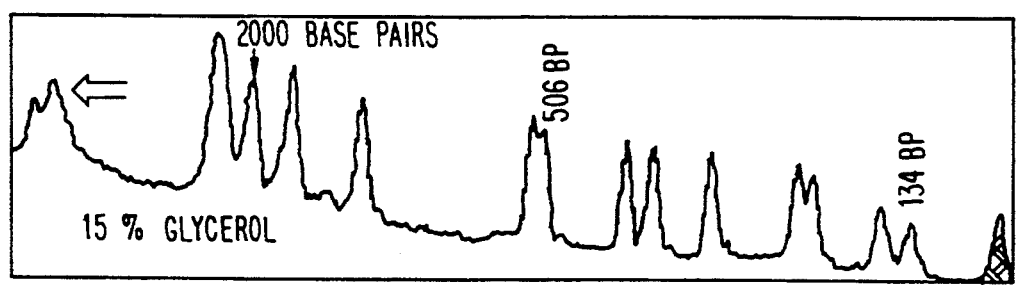
Figure 1E:
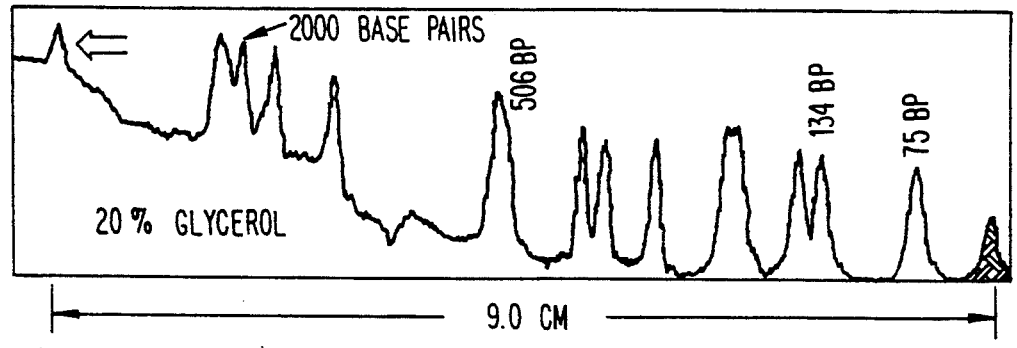
Figure 2:
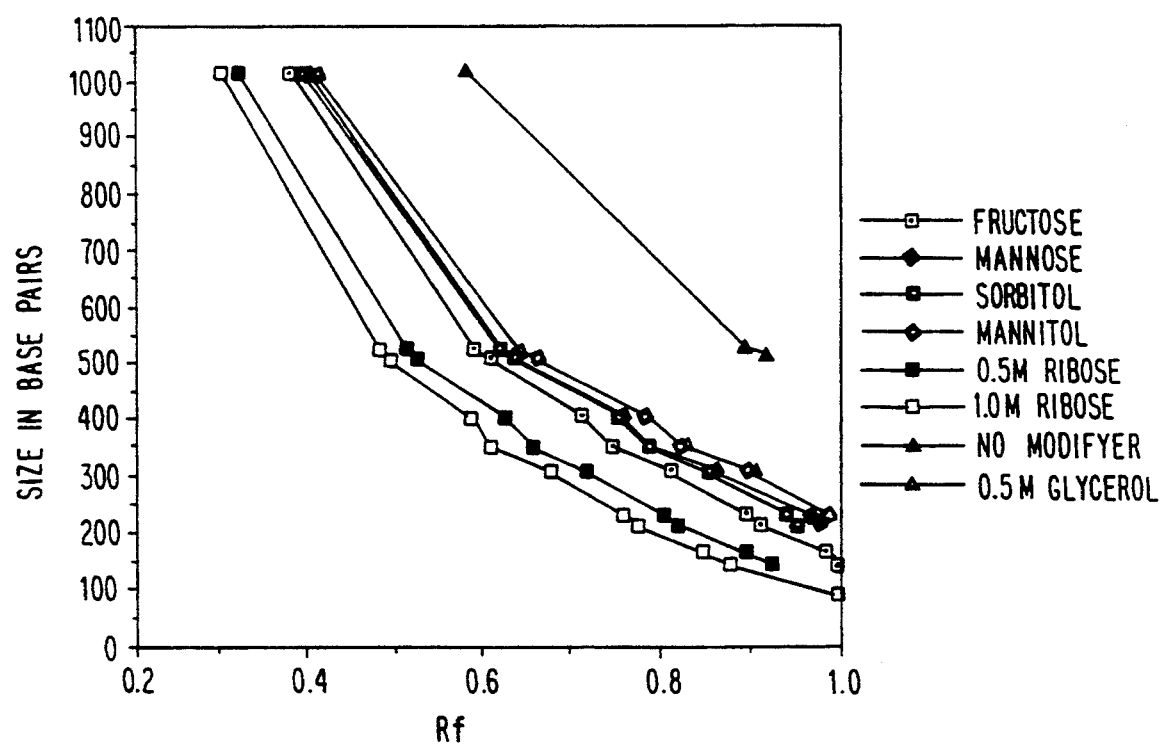
FIG. 2 shows the effect of different modifiers of polyacrylamide gel on the electrophoresis resolution of double stranded DNA, the size and base pairs of which vary.
Figure 3:
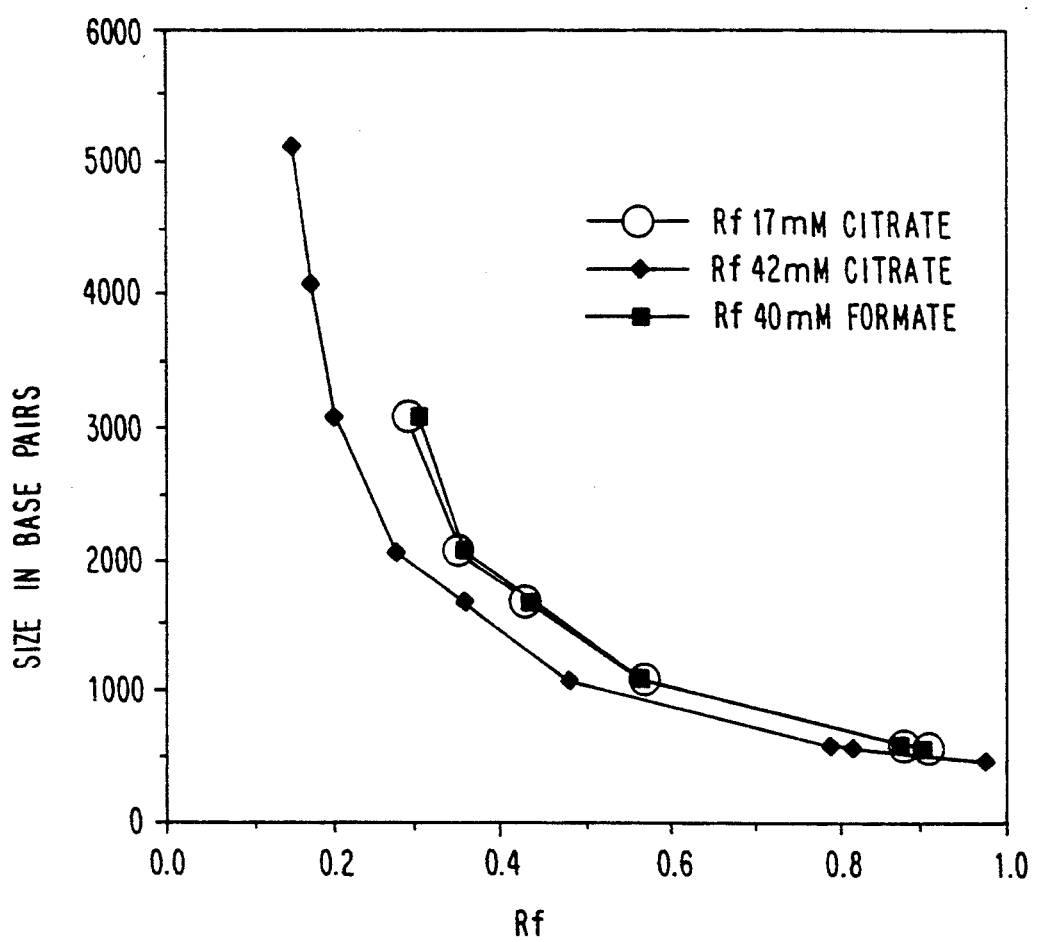
FIG. 3 shows the effect of ionic strength on the resolution power of an electrophoretic support.
Figure 4:
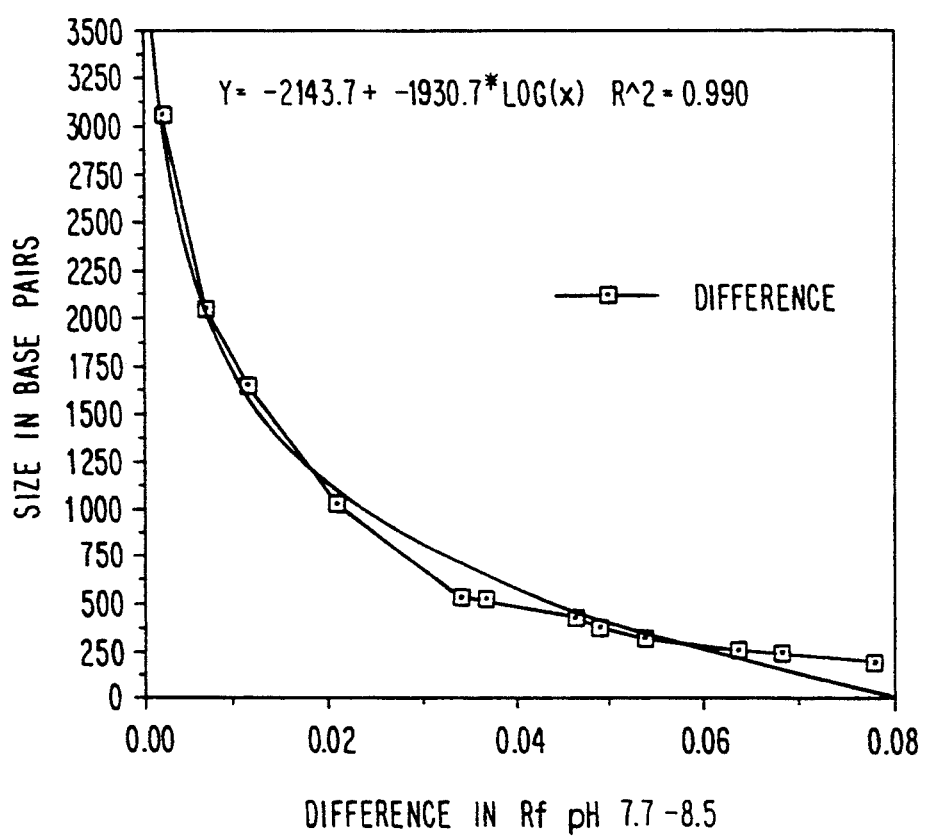
FIG. 4 shows the effect of pH on electrophoretic mobility of double stranded DNA of various sizes.
Figure 5:
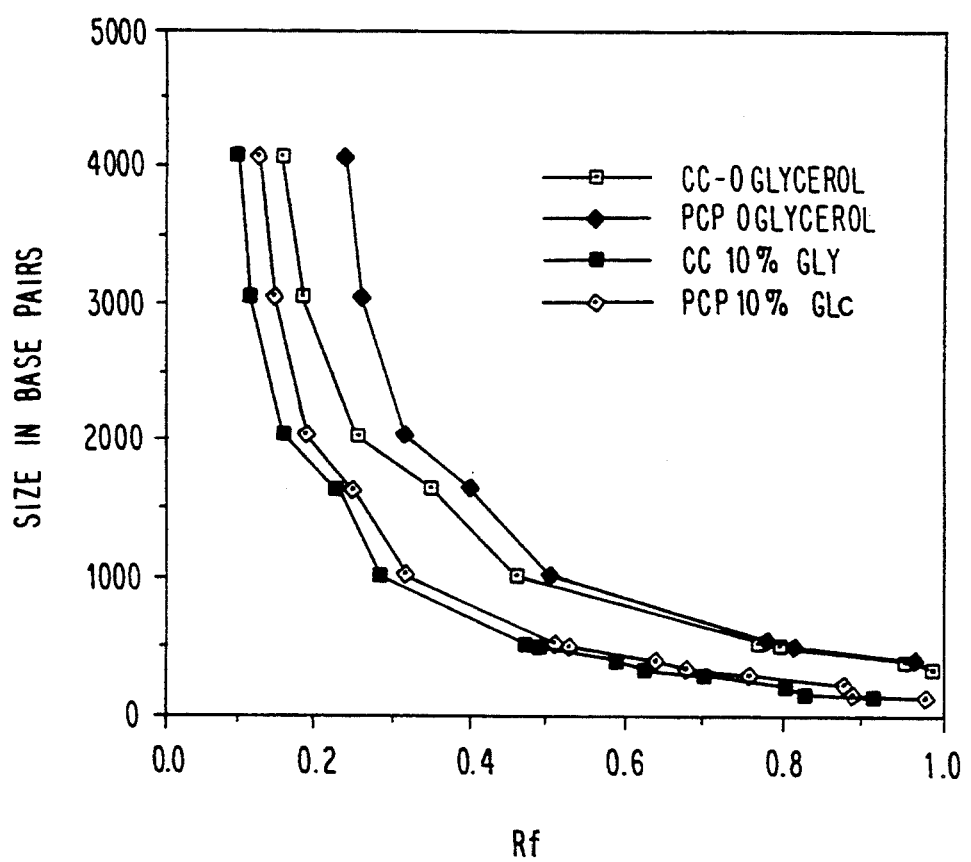
FIG. 5 shows the effects of constant current rs. pulsed constant power electrophoresis procedures in combination with matrix modified and non-matrix modified electrophoretic support.
Figure 6:
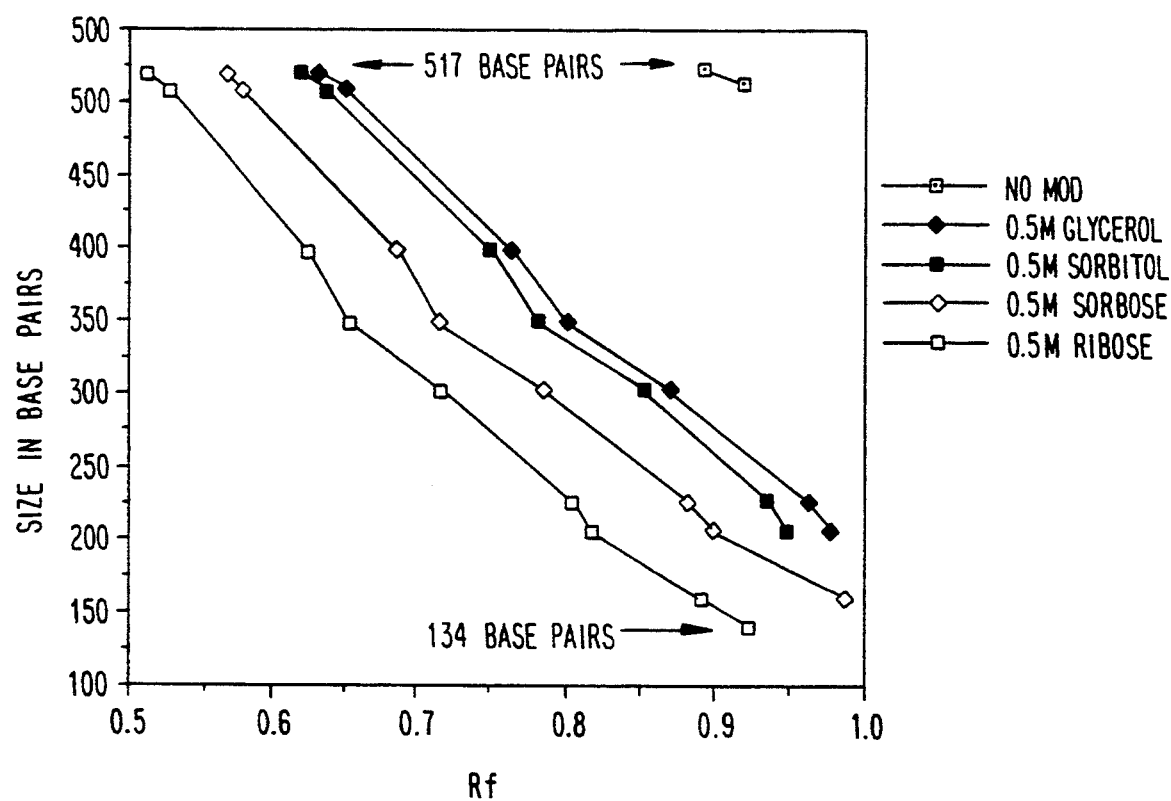
FIG. 6 shows the effects of structure modification of matrix modified electrophoretic gels in combination with discontinuous electrophoresis and the effects of resolving double stranded DNA varying in size.
Figure 7:
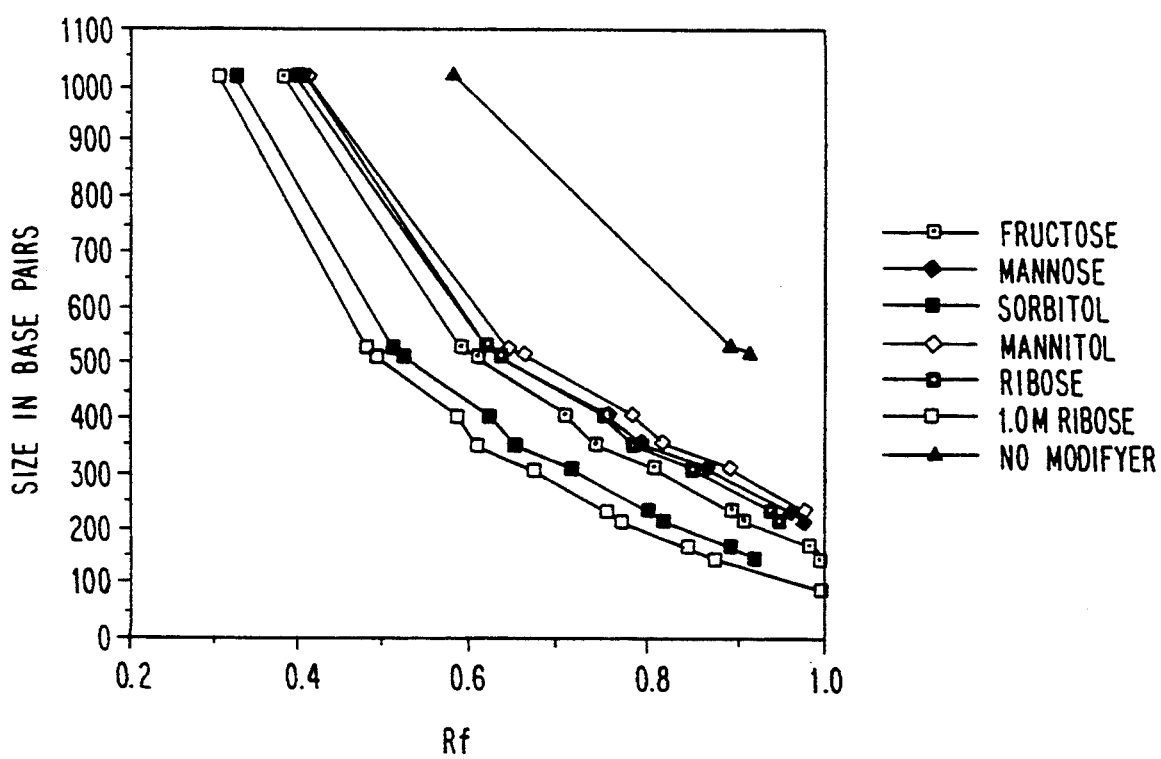
FIG. 7 shows the electrophoretic effects of monosaccharide structure on RF of variously modified electrophoretic supports on double stranded DNA.
Figure 8:
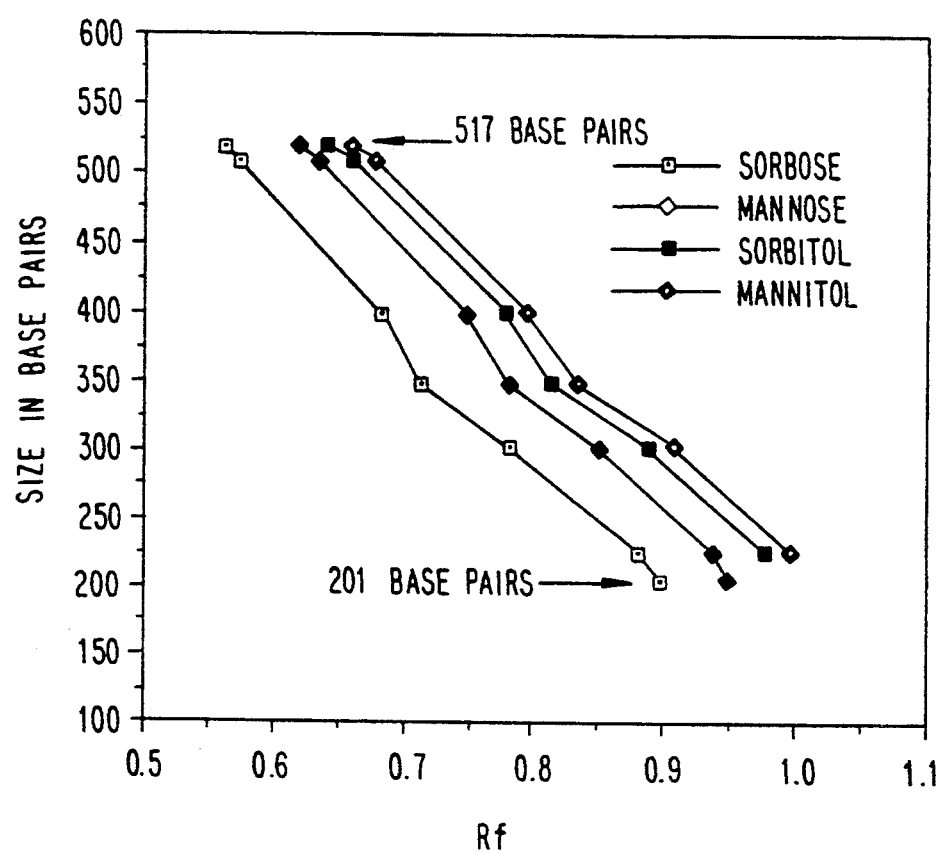
FIG. 8 shows the effect of chain and pyranose ring structures as matrix modifiers of electrophoretic support and their effect upon the resolution of double stranded DNA.
Figure 9:
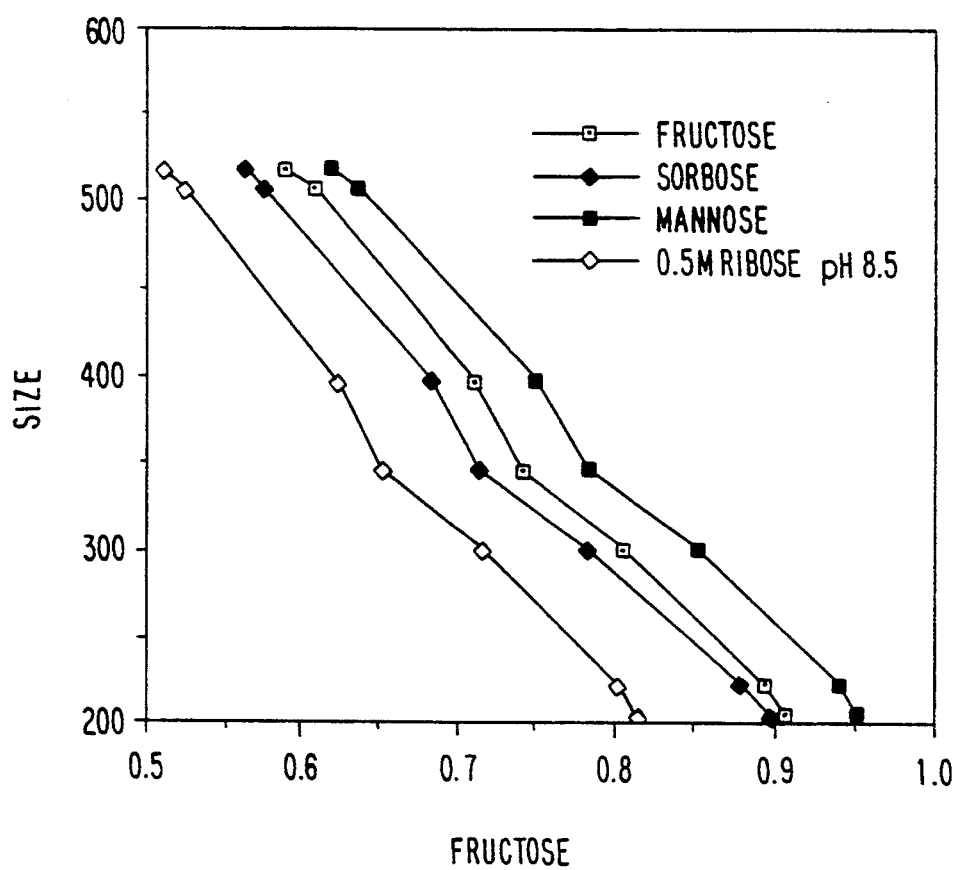
FIG. 9 shows the effect of pyranose and furanose ring structures as modifiers of electrophoretic supports and their effect on the resolution of double stranded DNA of varying sizes.
Figure 10:
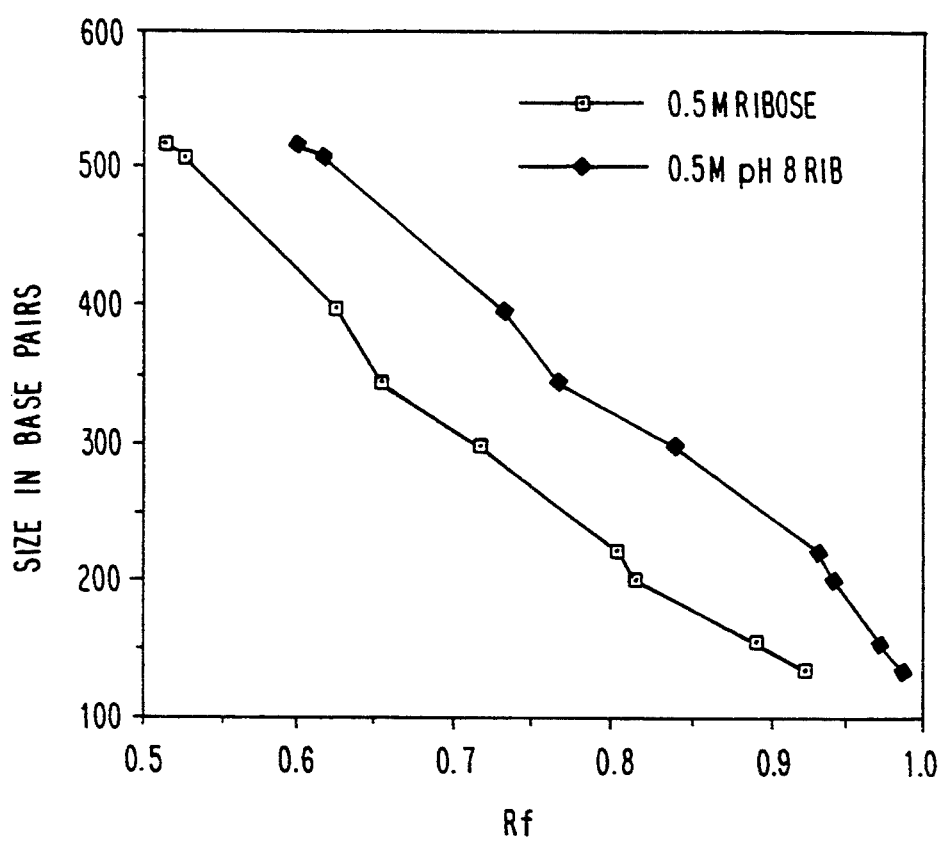
FIG. 10 shows the pH effect on the resolution of nucleotides of varying sizes using a ribose modified polyacrylamide electrophoretic support.
Figure 11:
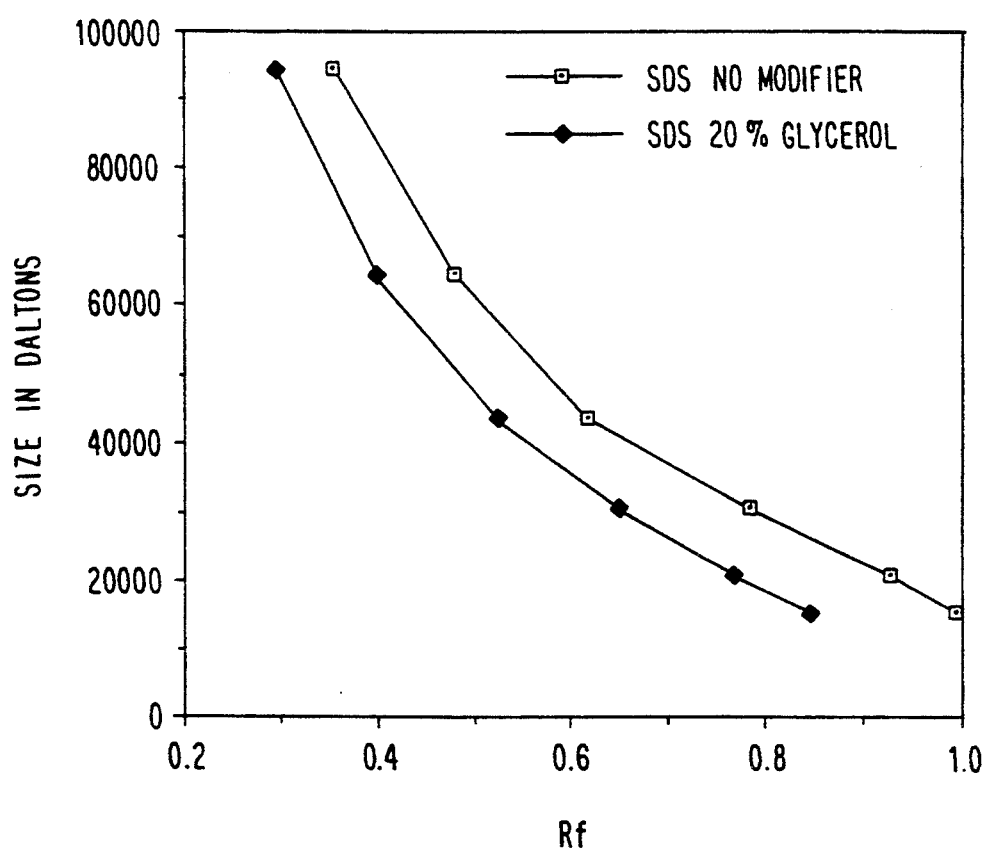
FIG. 11 shows the effect of glycerol on SDS treated protein molecular weight standards.

The present invention provides a process for modification of polyacrylamide electrophoretic support medium for the separation of a wide variety of sizes of macromolecules such as polypeptides and polynucleotides.

The present invention involves "matrix modification" of electrophoretic support media. Simple modification of matrices allows for multiple types of electrophoretic separation, such as continuous, multizonal electrophoresis and isoelectric focusing and size determination of proteins and nucleic acids using a single given pore size of support, whereas previously a multiplicity of pore-sized support media were required for the same purposes to accomplish separations.

In addition, discontinuous buffer systems, which produce a moving boundary, are used to sharpen sample component zones initially to produce maximal resolution of the electrophoretically-separated macromolecules. The term "sharpen sample component zones" refers to an increased separation of and definition of similar components in discrete zones or areas on the support. Resolution can also be improved by the use of "Good" zwitterionic buffers as trailing ions. These buffers contain both positive and negative ionizable groups. Second and tertiary amines provide positive charges, while sulfine and carboxylic acid groups provide the negative charges. These biological buffers are useful in the pH range of 6.0 to 9.0 and increase the resolving power of the electrophoretic system for nucleic acid fragments ranging from about 50 base pairs to about 4,000 base pairs. The resolution depends on the buffer used. The buffers and the pH ranges may be changed in order to modify the resolving power depending upon the particular macromolecules that need to be resolved.

MOPSO [3-[N-Morpholion]-2-hydroxypropanesulfonic acid],
GLYCYLGLYCINE [$H_2NCH_2CONHCH_2CO_2H$],
TAPSO [3-[N-tris(Hydroxymethyl)methylamino)-2-hydroxypropanesulfonic acid],
TRICINE [N,-TRIS(hydroxymethyl) methylglycine],
BICINE [N,N-bis(2-hydroxyethyl)glycine],
EPPS [N-2-Hydroxyethylpiiperazine-N'-3-propanesulfonic acid],
HEPPSO [N[2-Hydroxyethyl]piperazine-N'-[2-hydroxypropanesulfonic acid],
HEPES [N-2-hydroxyethyl]piperazine-N'-2-ethanesulfonic acid],
BES [N,N-bis-(2-hydroxyethyl)-2-amino-ethanesulfonic acid],
TAPS [3-{(tris-[hydroxymethyl]-methyl)-amino}-propanesulfonic acid],
TES [3-{tris[hydroxy-methyl]methyl)-amino}-ethanesulfonic acid],
DIPSO [3-[N,N-bis(2-Hydroxyethyl)amino]-2-hydroxy-propanesulfonic acid],
MOPS [3-(N-Morpholino)propanesulfonic acid],
MES [2-(N-morpholino)-ethanesulfonic acid],
POPSO [Piperazine-N,N'-bis-[2-hydroxy-propanesulfonic acid],
PIPES [Piperazine-N,N'-bis(2-ethanesulfonic acid)],
ACES [N-(2-acetammido)-2-aminoethanesulfonic acid], and
CHES [2-(N-Cyclohexylamino)ethanesulfonic acid].

Treating the support matrix with compounds selected from the group consisting of alcohols, polyols, or monosaccharides (matrix modifiers) retards the migration of the nucleic acids that would normally not unstack from a moving boundary in untreated matrices of the same pore size while the use of glycerol similarly affects proteins. Modifiers, such as methyl alcohol, glycerol, ethylene glycol and its derivatives, or monosaccharides such as sorbose, sorbitol, mannitol, mannose, fructose and ribose are preferred for nucleic acids and glycerol is preferred for proteins.

Moreover, increasing the concentration of appropriate modifiers in a wide range of buffer ionic strengths, causes a reduction in the relative mobility (defined as the distance travelled by a macromolecule divided by the distance travelled from the origin by the moving boundary).

Systems may be produced where unstacking is accelerated in the presence of a increasing amount of a given modifier proving advantageous in the separation of a complex mixture of macromolecules, an example of which might be the improved resolution of the smaller DNA fragments required in DNA sequencing gels, or alternatively in an SDS molecular sizing separation.

In accordance with the present invention, there is disclosed a method for rendering the matrix of single type or pore size polyacrylamide electrophoretic support media useful for a multiplicity of types of electrophoretic separations of macromolecules and in the visualization process of various biological materials. It has been discovered that electrophoretic support media can be modified by adding specific amounts of one or more alcohols, polyols or monosaccharides–but not disaccharides. Monosaccharides where the hydroxyl group on the number one carbon has been blocked by a methyl group no longer act as modifiers. The matrix modifiers may be included within the gels during the casting process, soaked into precast gels, or placed in the rehydration mixture in the process of rehydrating rehydratable gels. Additionally, adjusting the pH of the modified matrix electrophoretic supports yields electrophoretic media having a surprising degree of resolution of a complex mixture of macromolecules.

An advantageous process according to the present invention is a single or multiple electrophoretic technique comprising (1) a first step comprising using an electrophoretic support and constant current, constant voltage or constant pulsed power electrophoresis to separate the macromolecules of similar sizes and electronic nature into zones (2) removing macromolecules from a particular zone on the first electrophoretic support, and (3) further resolving the macromolecules from a zone comprising (a) electrophoresis using a matrix modified support further modified with a buffer solution to increase the resolving power of the matrix support, or (b) pulsed constant power electrophoresis using a matrix modified support.

The polyacrylamide gels, useful in accordance with this invention, are made from acrylamide monomers which are polymerized in the presence of crosslinkers in accordance with conventional methods known to hose skilled in the art. These may be ultrathin-layer gel (100–400 thick), gels in capillaries (50–200$\mu$ in diameter) or gels up to 3 mm thick cast between two glass plates. Acrylamide gels may be gelled in the presence of a modifier or precast "empty" dried gels may be soaked in the modifier and appropriate buffer. In these materials, macromolecules may be separated under the influence of an electromotive force by the following characteristics of the macromolecule.

The size of each macromolecule is a function of its molecular weight usually expressed in daltons where proteins that range from 2000 to 1,000,000 daltons in size and nucleic acids from 300 to over 20 million may be separated by a variety of electrophoretic procedures on supporting media, for example, acrylamide or agarose. The former may be prepared in a variety of pore sizes or in a pore size gradient by altering the monomer concentrations and to a lesser extent, the crosslinking agent, which allows the individual macromolecules to be sieved during the electrophoretic separation. Thus, acrylamide gels may be prepared that will separate macromolecules ranging from 360 to 6 million dalton (nucleic acids) and 2500 to 800,000 dalton (proteins). On the other hand, the much larger pore size agarose gels can separate larger nucleic acids, but are much less efficient in the separation of the proteins where little or no molecular sieving is achieved with macromolecules in the size range of 2500 to 800,000 daltons.

Isoelectric focusing, a commonly used separation procedure, depends on charge separation alone where no sieving effect can be tolerated so that macromolecules will be separated in an electric field solely based on the isoelectric point of each component. At present, this procedure is limited to separation of protein macromolecules and may be carried out in large pore size polyacrylamide gels or in agarose rendered "charge-free" by the addition of locust bean gum to increase viscosity or treated with base to have a pI outside of the range of separation pH and, thus, overcome fixed charged of the medium that lead to the disruptive affects on resolution of the macromolecules by electroendosmotic flow.

Denatured proteins and native or denatured nucleic acids may be separated in acrylamide on the basis of their size. This is accomplished by either increasing the monomer concentration to about 10–20 % or by producing a gradient gel from, for example, 3 to 20% monomer concentration with acrylamide. The latter produces sequentially decreasing pore sizes in the support medium in the direction of migration of the macromolecules, effectively causing molecules to stop migrating as they reach a pore size limit too small for them to migrate further under the conditions of voltage gradient pH and charge present in the system. Altering the amount of agarose present in the support medium is used similarly.

Macromolecules may be separated in the first dimension by isoelectric focusing in a non-sieving medium and a gel containing the separated components then denatured and placed on a second dimension. Normally two-dimensional separations are not carried out in agarose support media.

The matrix of the polyacrylamide gel in the present invention is modified by the addition of specific compounds in the gel matrix rather than has been the case previously where the matrix itself, both with agarose and with polyacrylamide and its derivative polymers, has been changed to alter the pore size of the separating gel. Initial observations with glycerol added to the rehydration medium of rehydratable gels to condition the gel surface for hemoglobin loading led to the observation that the presence or absence of the glycerol affected the migration pattern of the red blood cell acid esterases. A major distinguishing feature of the present invention is the use of a buffer solution together with the matrix modified supports to unexpectedly increase the resolving power of the support. Also, the use of pulsed constant power electrophoresis together with the modified matrix increases resolving growth. It was similarly noted that DNA separations on the same hydratable gels that separation characteristics could be altered if varying amounts of glycerol were added to the gels, which was ascribed earlier to a viscosity effect.

Since glycerol viscosity is markedly affected by temperature one might expect that viscosity could affect the Rf of the macromolecules. However, experimental results did not show any differences in Rf over a range of from 10° to 30° C. in glycerol modified matrices. This, coupled with the fact that there were no effects on Rf from the addition of 10% amounts of the sucrose and maltose 10 20° C., effectively rules out viscosity as the cause of differential separations observed in polyacrylamide gels.

In actuality, the effect of Rf retardation by matrix modification on two major mammalian macromolecules, glycoproteins and nucleic acids, has been shown to be different. Retardation of double stranded DNA is effected in increasing order by methyl alcohol, ethylene glycol, glycerol, sugar alcohols such as mannitol and sorbitol, hexoses in the form of pyranose rings, and most effectively fructose and ribose in the form of a furanose ring structure. Sucrose and maltose have absolutely no effect on the Rf of nucleic acids. The observations that disaccharides show no Rf effect, the difference in Rf in the cistrans relationship of hydroxyl groups in mannitol and sorbitol and the Rf effects of pyranose and furanose ring structure indicate that structure, particularly the hydroxyl on the #1 carbon atom modification and steric fit play a major role in the observed Rf retardation affects with nucleic acids.

On the other hand, the Rf of native and SDS denatured proteins is most affected by glycerol and not at all by the monosaccharides in their ring or alcoholic forms. Similar to observations on nucleic acids, disaccharides such as sucrose and maltose have no effect on the Rf of proteins.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

We claim:

1. A method of increasing resolution and decreasing mobility of polynucleotides on an electrophoretic support for conducting electrophoresis comprising:
    adding to an electrophoretic support for conducting electrophoresis, a polynucleotide resolution increasing concentration of a compound selected from the group consisting of alcohols, polyols, and monosaccharides in the presence of an ionic buffer comprising an ion selected from the group consisting of sulphate, chloride and phosphate ions of a pH of range 6–9, wherein increased resolution and decreased mobility of said polynucleotide on said electrophoretic support results.

2. A method according to claim 1, wherein said ionic buffer is selected from the group consisting of
    EPPS (N-2-hydroxyethylpiiperazine-N'-3-propanesulfonic acid),
    HEPPSO (N(2-Hydroxyethyl)piperazine-N'-(2-hydroxypropanesulfonic acid),
    HEPES (N-2-hydroxyethyl)piperazine-N'-2-ethanesulfonic acid),
    BES (N,N-bis-(2-hydroxyethyl)-2-amino-ethanesulfonic acid), TAPS (3-{(tris-(hydroxymethyl)-methyl)-amino-}-propanesulfonic acid), TES (3-{tris(hydroxy-methyl)methyl)-amino}-ethanesulfonic acid), DIPSO (3-(N,N-bis(2-Hydroxyethyl)amino)-2-hydroxypropanesulfonic acid), MOPS (3-(N-Morpholino) propanesulfonic acid), MES (2-(N-morpholino)-ethanesulfonic acid), POPSO (Piperazine-N,N'-bis-(2-hydroxy-propane-sulfonic acid), PIPES (Piperazine-N,N'-bis (2-ethanesulfonic acid)), ACES (N-(2-acetammido)-2-aminoethanesulfonic acid), and CHES (2-(N-Cyclohexylamino)ethanesulfonic acid).

3. A method according to claim 1, wherein said alcohols are selected from a group consisting of methyl alcohol, glycerol, ethylene glycol, or an ethylene glycol derivative with a hydroxyl group on the number one carbon.

4. A method according to claim 3, wherein said polypeptide resolution modifying concentration of a compound is about 1% to about 20% glycerol.

5. A method according to claim 1, wherein said monosaccharides are selected from the group consisting of sorbose, sorbitol, mannitol, mannose, fructose and ribose with a hydroxyl group on the number-one carbon atom.

6. A method according to claim 1, wherein a polynucleotide to be separated on said electrophoretic support is DNA having from about 5000 to about 10,000 base pairs and electrophoresis used to separate the polynucleotide is pulse constant power electrophoresis.

7. A method according to claim 1, wherein said electrophoresis is constant current electrophoresis.

8. A method according to claim 1, wherein said electrophoresis is constant voltage electrophoresis.

9. A method according to claim 1, wherein said electrophoresis is constant power electrophoresis.

10. A method according to claim 1, wherein said electrophoretic support is an ultra-thin layer polyacrylamide gel.

* * * * *